(12) United States Patent
Nielsen et al.

(10) Patent No.: US 8,626,305 B2
(45) Date of Patent: Jan. 7, 2014

(54) SYSTEM FOR STIMULATION OF NERVES

(75) Inventors: Ricky Lindgaard Nielsen, Nibe (DK);
Michael Høyer, Aalborg SV (DK);
Morten Hansen, Storvorde (DK)

(73) Assignee: Neurodan A/S, Aalborg SV (DK)

( * ) Notice: Subject to any disclaimer, the term of this patent is extended or adjusted under 35 U.S.C. 154(b) by 0 days.

(21) Appl. No.: 13/704,485

(22) PCT Filed: Jul. 11, 2011

(86) PCT No.: PCT/DK2011/050272
§ 371 (c)(1),
(2), (4) Date: Mar. 13, 2013

(87) PCT Pub. No.: WO2012/003840
PCT Pub. Date: Jan. 12, 2012

(65) Prior Publication Data
US 2013/0211474 A1    Aug. 15, 2013

(30) Foreign Application Priority Data

Jul. 9, 2010 (DK) .......................... PA 2010 00614
Jul. 9, 2010 (DK) .......................... PA 2010 00615

(51) Int. Cl.
*A61N 1/00* (2006.01)

(52) U.S. Cl.
USPC .......................................... 607/49

(58) Field of Classification Search
USPC .......................................... 607/49
See application file for complete search history.

(56) References Cited

U.S. PATENT DOCUMENTS

| 7,403,821 B2 | 7/2008 | Haughland et al. |
| 2009/0069865 A1 | 3/2009 | Lasko et al. |

FOREIGN PATENT DOCUMENTS

WO    2004087256 A1    10/2004

OTHER PUBLICATIONS

PCT International Search Report for PCT International Application No. PCT/DK2011/050272, mailed Sep. 19, 2011.

*Primary Examiner* — Christopher D Koharski
*Assistant Examiner* — Nadia Ahmad
(74) *Attorney, Agent, or Firm* — Holland & Hart LLP (57) ABSTRACT

In a system for stimulation of nerves comprising implanted electrodes, an external to the system trigger device is equipped with a sensor and a transmitter for wirelessly broadcasting a signal to be received by a pulse generator for generating a pulse pattern to be forwarded to the at least one electrode implanted in the corpus of the living being. Further the trigger device is equipped with means for detecting if the patient is walking or just standing pulling the weight from one leg to another and can thus determine if a stimulation sequence has to be performed.

15 Claims, 7 Drawing Sheets

SYSTEM FOR STIMULATION OF NERVES

TECHNICAL FIELD

The present invention is generally concerned with the art of electrical stimulation of nerves.

BACKGROUND OF THE INVENTION

Electrical stimulation of nerves or branches of nerves is known to be effective in the treatment of a variety of neurological disorders in living beings spanning from treatment of incontinence to gait disorders.

Treating gait disorders, especially correcting drop-foot, electrodes are placed in the proximity of the peroneal nerve or its branches. A pulse generator connected to the electrode generates a pattern of pulses to stimulate the nerve which will cause the foot dorsiflexor muscles to contract. Thus the foot will be lifted and it will be possible for the patient to swing the leg in a more natural manner. An example of a system for correction of drop-foot is known from U.S. Pat. No. 7,403,821 B2 to Neurodan A/S. The document covers the medical aspects and examples of various preferred embodiments are disclosed. For the triggering of the electrical stimulation of the nerve, according to the wanted reaction of the foot, the use of a heel switch is shown. Both the heel-off and heel-strike can be detected and used for input to the pulse generator in order to calculate and initiate the appropriate pulse pattern to be fed to the electrode. The heel switch can be connected to the pulse generator with electrical wires or the heel switch can include a wireless module for communicating the pulse generator. Normally, a heel switch is only arranged on one foot, the paralyzed foot or the fully functioning, and the pulse generator can be configured to synchronize the stimulation accordingly.

Using a wireless module is an advantage since connection wires in the area on the leg from the foot to above the knee can be omitted. Thus there is no possibility of cables being caught and damaged.

Anyhow a disadvantage can be seen in that a heel switch featuring a tactile switch for sensing the heel-strike and heel-lift events gives a very digital interpretation of the swing phase of the gait. Normally the activation of the switch requires only a low force corresponding to a low weight placed on the contact, since the trigger device should be suitable for use by all patients, without concern of the weight of the patient. If a person rests on the legs without having an active swing phase, the toggling of the tactile switch can lead to the triggering of nerve stimulation which will have an unwanted annoying effect. There seems to be room for an improvement of the system.

US2009/0069865A1 to Cooley Godward Kronish LLP describes a sensor device comprising a force-sensitive resistor and a microcontroller for receiving a signal containing the gait information from the sensor device. The microcontroller is further adapted for calculating a dynamic range and certain thresholds based on the dynamic range. Anyhow a disadvantage is seen in the sensor device having quite a high power consumption since the microcontroller will have to be constantly polling the signal from the sensor device thus having a rather high power consumption.

It is an object of the present invention to provide a trigger device for a system for stimulation of nerves, which gives an improved determination of the heel-strike and heel-off events and determination of when the person is performing a gait cycle and when the patient is resting on the legs. In addition a simple and power saving solution is wanted, in order to achieve extended battery lifetime.

This is provided with the present invention, according to claim 1, where the trigger device is equipped with switching means for sensing at least the events where a first threshold of load and a second threshold of load is exceeded.

In a first aspect, the present invention provides a system for stimulation of nerves including a programmable controller equipped with a pulse generator for generating a pulse pattern to be forwarded to at least one electrode implanted in the corpus of the living being and/or at least one electrode for surface stimulation of nerves or muscles, the controller being equipped with a wireless receiver for wirelessly receiving a broadcasted signal from a trigger device for adjusting the timing of the pulse pattern, the trigger device including a wireless transmitter for communicating with the controller, the trigger device is equipped with switching means for sensing at least the events where a first threshold of load and a second threshold of load is exceeded.

The switching means can in a first embodiment be mechanical activated electrical conducting switches. In the preferred embodiment the switching means are tactile switches that recover to the non activated position when the mechanical activation force is released.

More specific this is according to the invention provided by carrying out the trigger device to include switching means to indicate when at least two differentiated thresholds of load is met. Connecting the switches to a controller, a signal will be issued as input for the controller to record the event of toggling the switches. The event will be registered with regard to timing of the events in form of a recorded timestamp. If the first threshold is configured to present a weight less than the weight of the person and the second threshold is configured to present a weight close to or slightly over the full weight of the person, the toggling of the switches can picture the phases of the gait of the patient. For the sake of completeness, a person suitable for using the device could weigh between 40 to 160 kg and the thresholds should be calibrated accordingly to achieve the wanted measured response. It also has to be understood that during the gait swing phase, extra force is put into the swing, thus when the foot strikes the under laying surface the extra force is perceived as an extra weight, thus a resulting weight larger than the weight of the person can be measured. The timing between the events can thus indicate if the person is performing a gait swing phase or resting on both feet. More expediently, during walk, the full weight of the person will produce a steep weight curve, thus the gait swing phase is indicated by a short timing between the toggling of the switches. When the person rests on both feet, and is moving the weight between the two legs, one switch will be toggled and the time interval until the second switch is toggled is significantly longer than the timing in a gait swing phase, if the second switch is toggled at all.

A general purpose system with specific weight thresholds is preferably capable for being used by all patients, independent on the weight of the patient. An example of values for the first threshold could be thirty kilo grams and for the second threshold sixty kilograms. However, it can be foreseen that it is necessary to provide more versions of the trigger device each matching a specific weight segment of patients. Several ways of adapting a general purpose trigger device to all patients can be foreseen. One way of adapting the threshold to the specific patient can be by attaching a flexible plate, preferably having an adhesive on at least one surface adapted to face towards the part of the device where the switches are arranged. Since the plate is flexible some of the load is bypassed and the thresholds of the switches are increased. More plates can be introduced with different flexibility for adapting the thresholds of the switches to the individual patient. Color coding the plates according to the increase in weight or threshold of load, will serve in an easy way to aid the user in choosing the right adaptor plate.

Arranging a trigger device on both feet, and carrying out the pulse generator in a way where it can receive and process the data received from both trigger devices in order to correspond the events in the gait cycle is advantageous since taking the events on both feet into account will give a better picture of the current state of movement. Thus a more reliable determination of movement or resting on the feet can be made.

In a preferred embodiment, the trigger device includes at least one piezo electrical sensor for detecting the events in the gait phase. More expediently, the piezo electrical sensor will serve to provide a signal from which it is possible to determine not only the events of heel-strike and heel-off but also the events where the load exceeds certain thresholds as e.g. a first threshold of load or a second threshold of load. In order to provide a system which still consumes low power, it includes a number of switches, at least one, electronic switches which are arranged in a voltage divider circuit. The voltage divider circuit is supplied with a signal from a sensor which in a preferred embodiment is a piezo electrical sensor. The piezo electrical sensor is preferred since it generates a signal in itself and do not need any reference or supply voltage. This is contrary to passive sensors as e.g. FSR's. However, it is appreciated if the use of passive sensors using a reference voltage is also covered by the invention. As the switches can be implemented with C-MOS comparators, standby power-consumption can be kept to an absolute minimum. The raw signal from the piezo electrical sensor or a first threshold switch of the voltage divider could be used to trigger an interrupt on the micro controller to start calculating the status of the gait. This will enable the microcontroller to enter a sleeping mode with low power consumption when the piezo electrical sensor does not provide any signal or just a very low signal, or when the task to be done when pulling the interrupt has been performed. In an appreciated embodiment each voltage level in the divider circuit represented by the toggling of the corresponding electronic switch will be forwarded to the microcontroller and serve as an interrupt signal. The interrupt will not only be active on the positive edge of the signal of the electronic switch but also during the negative going transition. In this way the microcontroller can calculate the time between the rise and fall of the signal at the specific threshold level. This information is important for determining the gait state of the patient by comparison with predefined profiles stored in the memory of the microcontroller. Since the interrupt is also active on the negative going edge of the signal from the electronic switch it is possible for the microcontroller to enter a sleep-mode where no or a minimum of power is consumed when the switch/es is/are toggled back to the relaxed or low position corresponding to the situation where there is no signal from the sensor. Care should be taken to implement the switches in a way that rejects bouncing as e.g. with suitable scaled Schmitt trigger inputs.

The energy content in the piezo electric sensor generated signal could in an embodiment be used for fully or partly powering the C-MOS comparators used for the electronic switches. In this way the standby consumption of the trigger device is reduced to a minimum when the trigger device is not being used as e.g. under storing conditions. In a further embodiment the energy from the piezo electric sensor can be forwarded to an energy storage e.g. in the form of a capacitor or rechargeable battery that can be a contributing source of electrical energy for the trigger device.

The generation of signals to represent the events and the generation of electric energy will only take place when the piezo electrical sensor is manipulated mechanically in a dynamic way. Thus arranging a piezo electrical sensor in the trigger device in a place where the weight of the person will mechanically manipulate the piezo electrical sensor, will only issue signals during the dynamic movement of the gait. The energy level of the signal will correspond to the physical impact on the sensor. Thus the transition from when no force is applied to the sensor and to the full weight of the patient is applied to the sensor, will generate a large signal. A patient resting on his legs, and putting the weight alternately on the right and left leg, will not be subject for generating a large signal. Additionally the pattern of the curve will be easily recognizable when compared to a typical curve for the gait swing phase of the walking patient and thus as a result of the signal processing, it can be determined if neuro stimulation has to be carried out or not. This is especially the case where the signal has been broken down into at least two, preferably more digital signals by a divider circuit as described in other embodiments of the invention.

Another aspect of the invention is that the use of a piezo electrical sensor will not only give the possibility of determining the heel-off and heel-strike event. Additionally it will be possible to measure the force pressure between the foot and the surface of the floor. Samples recorded over a time domain between the heel-strike and heel-off events will be valuable input for adjusting the electrical stimulation pattern to support a more natural gait swing phase.

As an improvement over a solution based on mechanical activated electrical conducting switches where the mechanical switching threshold should be selected specifically with each patient in mind, a solution using a piezo electrical sensor and electronic switches has the advantage that the threshold levels can be adjusted with the use of a configuration software program running, setting up the specific thresholds for the patient and storing the values in the memory. This of course will require that more switching thresholds are implemented in the divider circuit in order to provide the needed resolution. It is foreseen that several thresholds could be measured in order to follow the specific gait cyclus of the patient more accurate and act accordingly when needed with the appropriate neuro stimulation patterns to stimulate the nerve and achieve a more natural gait swing phase.

More expediently the heel-switch device will be able not just to provide data for determining the pattern of the electrical stimulation signal for the swing phase, but also to provide data on the orientation of the foot itself during the event where the foot strikes the ground. This can be achieved by placing a plurality of sensors in the heel-switch device to be monitoring the pressure towards the surface in distributed spots on the foot. It has to be understood, that the expression "on the foot" includes not just the area on top of the foot, but the full area on the skin surface surrounding the foot. Similarly the area covered under the foot should not be restricted to the heel area, but could be any area underneath the foot. Also the sides of the foot could be interesting positions for placing sensors, since some patients tend to bend the foot (banana shaped foot due to spasms) in a way where the foot strike often occurs on the side of the foot. A set of data with timestamps for the start and stop of the event and the level of pressure, provided on multiple spots under the foot will be valuable input for determining the angular orientation of the foot during the swing and gait phase, for a continuously adjustment of the electrical stimulation to form a more natural swing and gait phase. Especially appreciated is that the system with the use of data processing will be able to recognize certain patterns in the gait swing and adapt to the changing of speed of the gait cycles, e.g. step length and cadence of gait (Pace). Further examples of gait pattern recognition could be movement on stairs or backwards movements where appropriate stimulation patterns could be carried out for supporting the gait.

For protecting the piezo element against permanent damage, the amplitude of bending has to be limited. This can be achieved by placing the piezo element in a holding arrangement that limits to which extend the piezo element under normal conditions can be exposed to bending. Expressed in other terms, the tension on the piezo element must be limited to what is acceptable according to the specifications of the specific piezo element used and excess forces applied must be by-passed by the holding arrangement. Preferably the forces applied to the arrangement must be scaled between the holding means and piezo electrical sensor element in a manner where only a fraction of the forces is applied to the piezo element, such that full scale bending of the piezo corresponds to the maximum value of the force applied to the arrangement. An arrangement where a switch and a piezo electrical sensor are arranged together could be provided by adding a piezo electrical film on top of the dome of a tactile switch. Thus the switch would be able to provide a signal corresponding to the first threshold of weight and measuring the piezo electrical signal and comparing to a second threshold of weight, will be advantageous since it will be possible to provide a very compact and reliable device. In a further embodiment the switch will provide the interrupt signal for the microcontroller for the transition from sleep mode to the active mode where the actual thresholds are detected from the electronic switches measuring the signal from the piezo electrical sensor on the divider circuit.

The use of piezo electrical sensors for determination of the gait pattern of the patient, has an additional advantage since the energy generated by the piezo electrical sensor can be collected and used to fully or as a contribution cover the need of electrical energy for the trigger device.

For achieving the maximum generation of electrical power or maximum signal generation, the piezo electric sensor should during the operation not only be bended from its relaxed position to one of the extreme positions, but from one extreme position though the relaxed position and to the opposite extreme position, which would gain approximately double the energy or signal generation. This is achieved by including a bias spring in the holding arrangement in such a way that the spring puts a force on the piezo electrical transducer and bend it in direction towards a first extreme position. When the foot performs a ground strike action the pressure is put on the holding arrangement and forces the bending of the piezo electrical sensor towards the second extreme position. When the foot lifts from the ground, the bias spring will force the bending position back to the first extreme position of the piezo electrical sensor. Energy or a gait signal will thus be generated both when the patient wearing the device puts the foot to the ground and when the patient again lift the foot off the ground.

The activation of a switch, e.g. arranged in a heel switch device, will bend the dome acting as a biasing spring, and if a piezo foil is arranged on the dome the foil based piezo electrical sensor will be bended accordingly. The switch will reflect the heel-strike event and the piezo sensor will generate a signal that can be supplied to the electrical energy storage. When the heel-lift event occurs, where the pressure on the switch will be released, the dome shaped biasing spring will force the dome into its relaxed state thus performing a bending of the foil based piezo electrical sensor back to the initial state. During this transition, energy will be generated and forwarded to the electrical energy storage. Embodiments of the invention will be described with reference to the accompanying drawing, in which:

Figure 1:
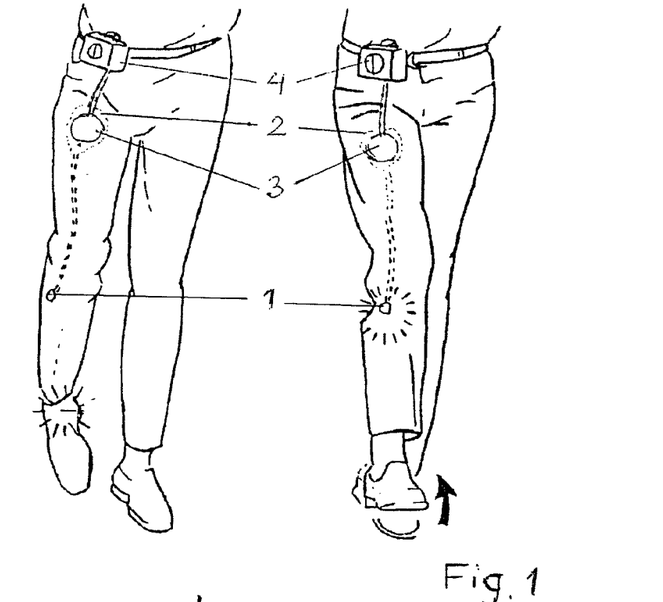
FIG. 1, shows an illustration of a leg region of a patient including a signal generator with antenna and implant with lead and electrode.
Figure 2:
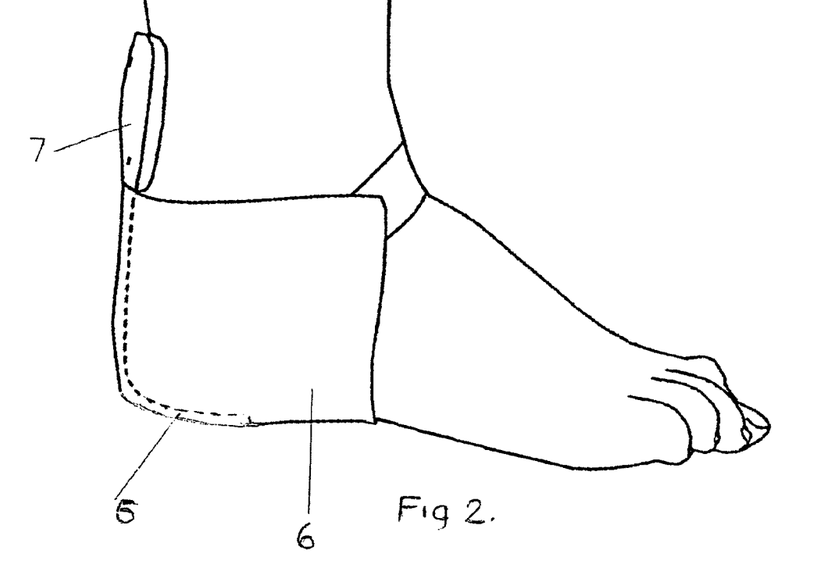
FIG. 2, shows an illustration of a foot with a sock for fixation of a trigger device in the form of a heel switch.

The system for electric stimulation of nerves shown in the drawing includes an implanted electrode 1 electrically connected to an implanted module 2. On the skin of the human body in the proximity of the implanted module 2 is arranged an antenna 3, the antenna 3 being connected to the signal generator 4. Thus the signal generator 4 supplies signals for inductively powering the implanted module 2 and providing pulses of electrical current to the implanted electrode 1. The electrode 1 is a CUFF electrode, a tubelike isolating fixture with a number of electrodes the fixture fully embracing the nerve to be stimulated at least over a distance of the length of the nerve. The specific nerve to be stimulated in the present application is the Peroneal nerve. Stimulating the nerve has the effect to cause the foot dorsiflexor muscles to contract. Thus the foot will be lifted and a more natural swing phase of the gait can be achieved. The stimulation signal must be synchronized with the gait of the patient, thus the need for a trigger that reflects a well defined event of the foot. The heel-strike and heel-off events are useful events for determining the gait cycle of the patient and can easily be obtained using a heel switch. It has to be noted that the term "heel switch" does not limit the application of the device to the position under the heel of the patient. The term is generally used for describing a trigger device serving as a switch that can be placed at any surface on the foot. To avoid wiring between the controller and the heel switch a wireless communication link is used. An example of a state of art heel switch 5 is shown in FIG. 2. The heel switch device is fixed to the foot with the use of a sock 6. Normally the trigger is equipped with a transmitter 7 and the signal generator 4 is equipped with a receiver. In addition the trigger device also includes a battery capable of supplying the trigger device with a flow of current for an extended period of more than a year.

Figure 3:
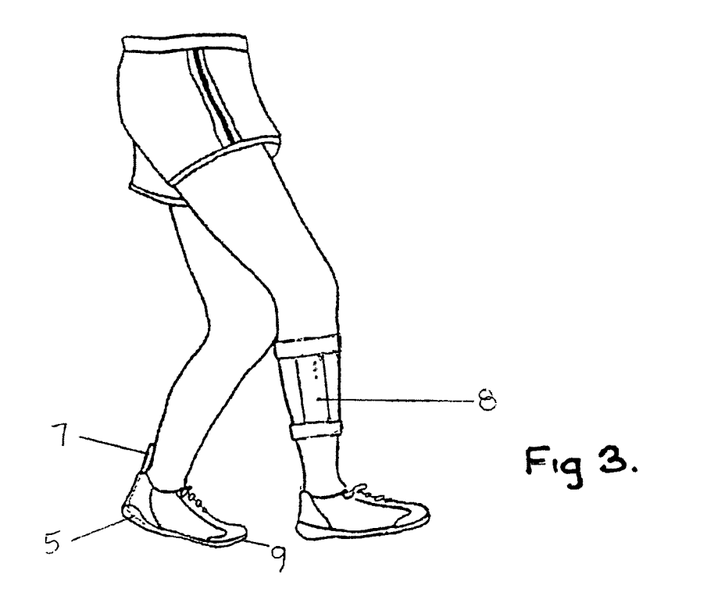
FIG. 3, shows an illustration of a leg region of a patient with a system for surface treatment of nerves.

The use of a wireless trigger device in the form of a heel switch is not exclusively intended for implanted systems for stimulation of nerves. Systems using surface stimulation of nerves in order to achieve the same result as the above mentioned implantable system may also comprise a wireless heel switch. FIG. 3 is showing a surface stimulator device 8 attached to the lower right leg with a wireless heel switch including a transmitter 7 and a heel switch 5 arranged in the shoe 9 on the left foot. It has to be understood that the choice of the left foot is just in order to explain the heel switch and is coincidental. A wireless heel switch could of course be arranged in connection with the left or right foot free of choice or with a wireless heel switch arranged with each foot, requiring that the receiver is able to handle two wireless heel switch devices simultaneously.

The way of communication and means for communication will not be further explained, but could be carried out using traditional radio transmitters and receivers or transponders. In the present example a standard radio transmitter and receiver is used for explaining the invention. The communication is following a pattern that is put down in a common protocol for data communication between the transmitter and receiver.

Figure 4:
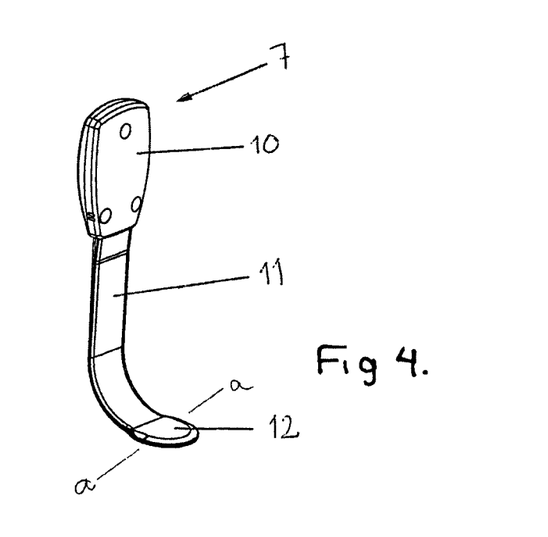
FIG. 4, shows an embodiment of a trigger device with a housing for the electronics and an elongated part for arranging the piezo electrical sensor in position under the foot.

An example of a trigger device is shown in FIG. 4, where the electronics is enclosed in the housing 10, the housing being equipped with an elongated connection part 11 for connecting the electronics to a piezo electrical sensor 12 arranged in the end of the elongated connection part. Protruding out of the shoe wear, the device will be less irritating to use by the patient, and a better radio connectivity between the transmitter and receiver can be achieved.

Figure 5:
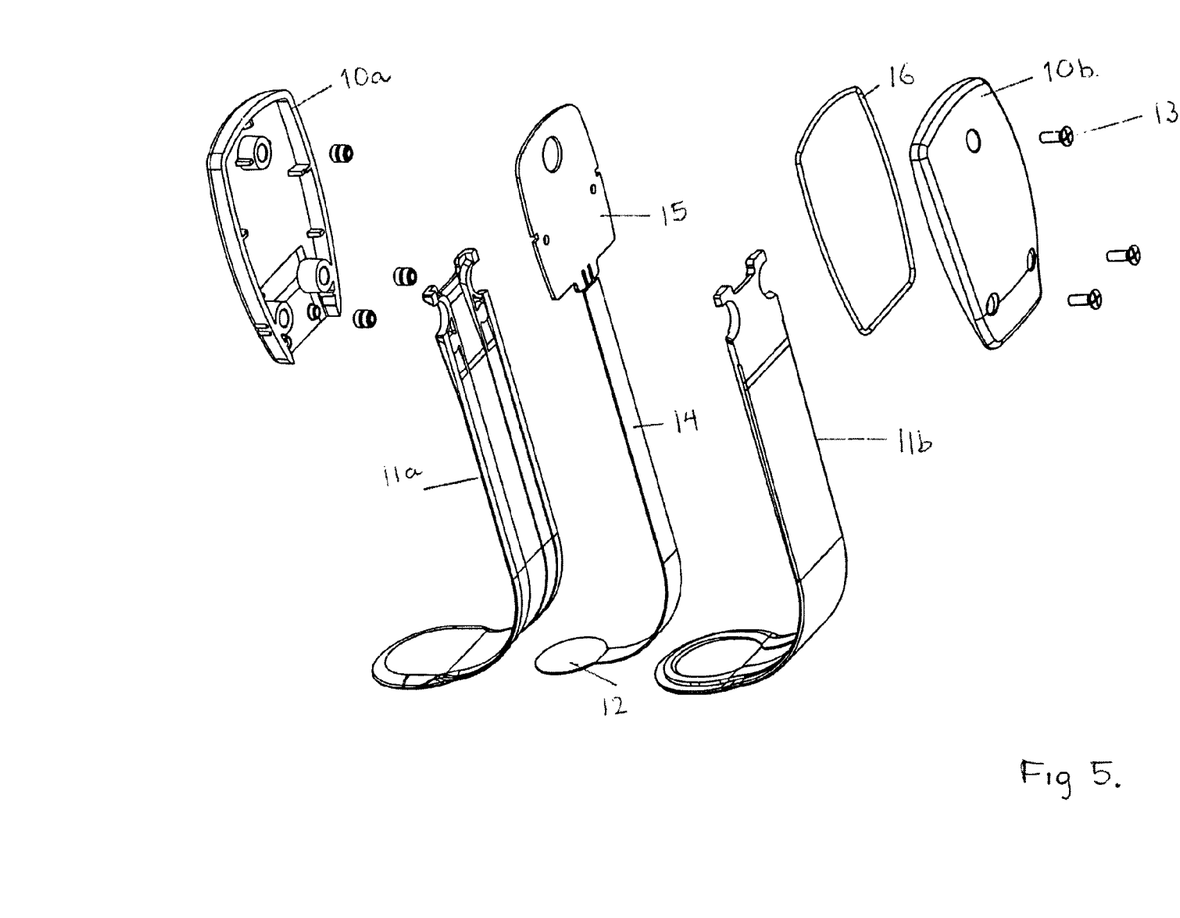
FIG. 5, is an exploded view of a trigger device with a piezo electrical sensor.

FIG. 5, shows the device of FIG. 4 in exploded view. The housing 10 consists of a first part 10a and a second part 10b that are assembled and locked together with the use of fastening means in the form of screws 13. For the sealing of the housing against penetration of dust or liquids, a gasket 16 is inserted between the two housing parts 10a, 10b. The elongated connection part 11 is made of two parts, a first connection part 11a and a second connection part 11b formed as a receiving and guiding means for enclosing a flexible printed circuit board 14. The flexible printed circuit board is, with its electrical connections, in one end connected to the piezo electrical sensor 12 and in the other end connected to a printed circuit board 15 on which the electronic circuits for the controller, wireless transmitter and energy harvester are arranged. The printed circuit board 15 is adapted to fit into the housing 10. The housing 10 also has supporting means for fixing the printed circuit board in a fixed position in the housing 10. For the sake of completeness a further embodiment of the invention is substituting the piezo electrical sensor with two or more switches, arranged side by side or stacked on top of each other in such a way that the switches will be activated one by one depending on the load put upon them. This means that when the full weight of the person is put on the switches they may all be activated, but if the person is resting on both legs or moving the weight from one leg to another a fewer number of switches might be activated.

Figure 6:
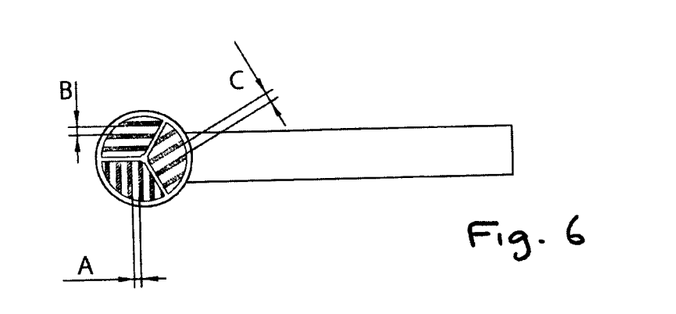
FIG. 6, shows a trigger device with a arrangement of three switches in one device.

An embodiment of a heel-switch having three switches arranged side by side is shown in FIG. 6. The areas with the width A, B and C represent the spacer between the contact points. The wider the spacer the more force is needed to activate the switch. In this way a heel-switch is provided that features more thresholds for activation. Thus it is possible from the state of the switches to determine if the person is walking or just standing or shifting the weight between the legs and accordingly if needed initiate an electrical nerve stimulation session.

Figure 7:
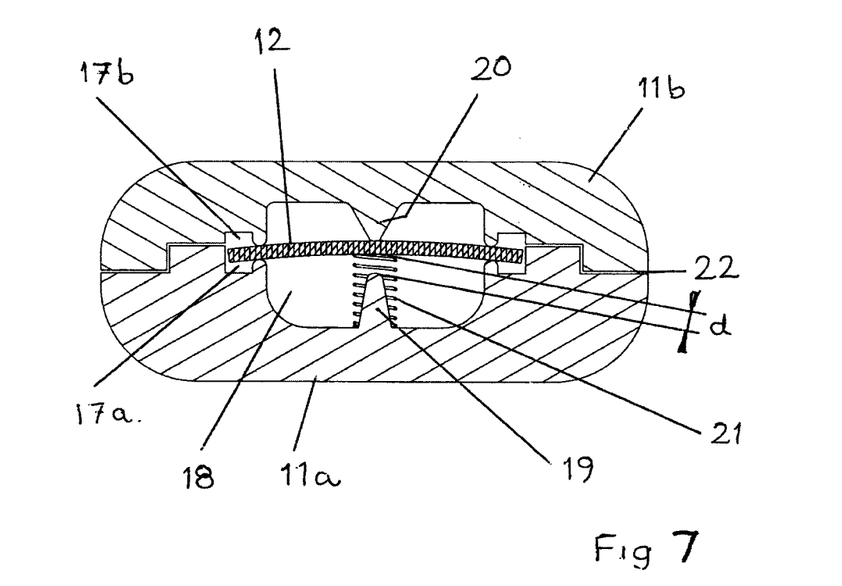
FIG. 7, shows a cross section of the holding arrangement that limits the bending of the piezo electrical sensor.

A detail of the receiving means for the piezo electrical sensor that cannot be seen in FIG. 5 is shown in FIG. 7, which is a cross section a-a of the elongated connection part 11. In the first connection part 11a is formed a recess 16 for receiving the piezo electrical sensor. For the understanding of the invention it has to be understood that the piezo electrical sensor used is the disc shaped, substantially flat foil based types where a substrate of piezo electrical crystals are forming a layer on the foil. The recess is forming a bed for keeping the outer diameter of the piezo electrical sensor in a fixed position in relation to the first connection part 11a. The first connection part 11a also features a cavity beyond the center point of the piezo electrical sensor, the depth of the cavity is forming a stop for the measure of bending the piezo electrical sensor in one direction. A second connection part 11b is adapted to be a counterpart for the first connection part 11a. It serves firstly to form a stop to keep the outer diameter of the piezo electrical sensor in its fixed position in the closed connection part 11. The second connection part 11b has a cavity that allows the center point of the piezo electrical sensor to bend in the upwards direction. A border for the bending is formed by an arm that serves as a stop. Additionally as a counterpart, a spring is inserted in the first connection part 11a and puts a bias pressure on the piezo electrical sensor 12 which in the relaxed position of the trigger device will be bended to meet the stop formed in the second connection part 11b. Putting a weight on the connection part (e.g. the weight of a person) will force the arm down on the center point of the piezo electrical sensor and it will be bend accordingly. Depending on the strength of the force and the spring arrangement in the connection part, the piezo electrical sensor might be bend to the maximum limit and be hindered for further bending when the stop is reached. In this way the piezo electrical sensor is protected against destructive bending. Since the force will only be applied from one direction, the arrangement with the bias spring will produce a longer replacement of the center of the piezo electrical sensor and thus be able to produce a larger signal. Thus a higher resolution of the measurement can be achieved, thus leading to a better representation of the phases of the gait swing pattern.

Figure 8:
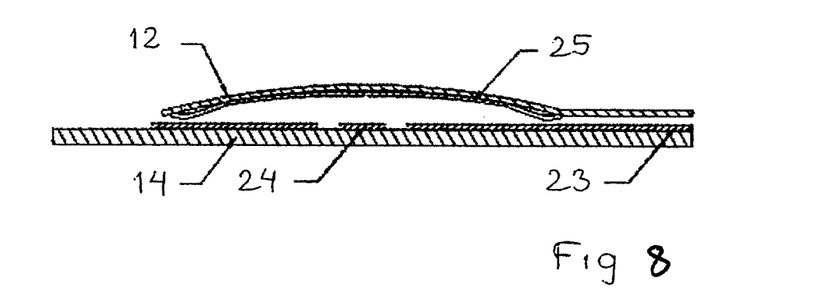
FIG. 8, shows an embodiment of the trigger device featuring a piezo electrical sensor and a tactile switch.

Another embodiment is shown in FIG. 8 featuring a more simple and compact design that arranges and integrates a tactile switch and a piezo electrical sensor in one device. The flexible printed circuit board 14 is equipped with a tactile switch comprising a first connection point 23 carried out on the flexible printed circuit board 14 and a second connection point 24 equally carried out on the flexible printed circuit board 14. The connection points are routed on the flexible printed circuit board 14 with connection lines for electrical connection with the controller on the printed circuit board 15. The controller determines the heel-strike and heel-lift events on the transitions of the tactile switch. For connecting the connection points in case of heel-strike, a dome shaped contact component 25 is arranged in position over the connection points 23, 24 and when the switch is activated by pushing the dome shaped contact component in contact with the connection points, the electrical connection between the connection points are maintained. Since the dome shaped contact component is flexible having the qualities of a spring, the contact between the connection points 23, 24 will be lost when the force on the dome shaped contact component vanish as e.g. when the foot is lifted off the ground (heel-lift) during the gait swing phase. A piezo electrical sensor 12 formed on a film is attached to the dome shaped contact component in such a way that the sensor is bend accordingly to the bending of the dome shaped contact component. Thus the toggling of the dome will also generate a signal on the piezo electrical sensor, the signal being forwarded to the electrical energy storage for supply of the controller and transmitter. More layers of piezo foil e.g. arranged stacked, can be foreseen to cover the dome in order to provide a higher and more detailed output signal. Additionally, more parallel sensors will safe-proof the system against a failure in one of the sensors. It will be appreciated if the invention is not limited to the simultaneous use of a switch. The dome shaped contact component 25 could be used only for the purpose of providing a biasing spring for the piezo electrical sensor 12 without any electrical switching means. It has to be understood that the device of FIG. 8 will further benefit of being encapsulated and protected, e.g. by casting into a suitable block of silicone.

As seen in the embodiments of the invention, the signal expressing the heel-strike and heel-lift to be forwarded by the trigger device can be produced by a switch that is toggled by the weight of the person. The presence of the piezo electrical sensor is taking the need away for the switch for determining the heel-strike and heel-lift events. However, for the sake of minimizing the current consumption, the switch could still be used as a wake up signal for the microcontroller, the microcontroller when activated will start monitoring the signal from the piezo electrical sensor in order to determine if nerve stimulation has to be initiated. More detailed the microcontroller will monitor the state of additional switches as e.g. stacked or parallel switches adapted to be placed on the foot. More appreciated the switches will provide interrupt signals to the microcontroller for performing a storing of timestamp information and the programmed action to be done, which avoids polling and minimizes runtime of the microcontroller and lowers power consumption. Thus the microcontroller can predominantly enter a sleep mode where a minimum of power is consumed. The microcontroller will then according to the interrupts send information to the pulse generator if and when neurostimulation has to be initiated.

It is also foreseen that it is possible to use one piezo electrical sensor, e.g. one or more layers of the stacked foil, for supplying energy and one piezo electrical sensor, e.g. one or more layers of the stacked foil, for providing information on the heel-strike and heel-lift events. In an embodiment featuring only a single piezo electric sensor it would be possible both to provide signaling on gait events and generate a contribution to the energy supply.

Figure 9:
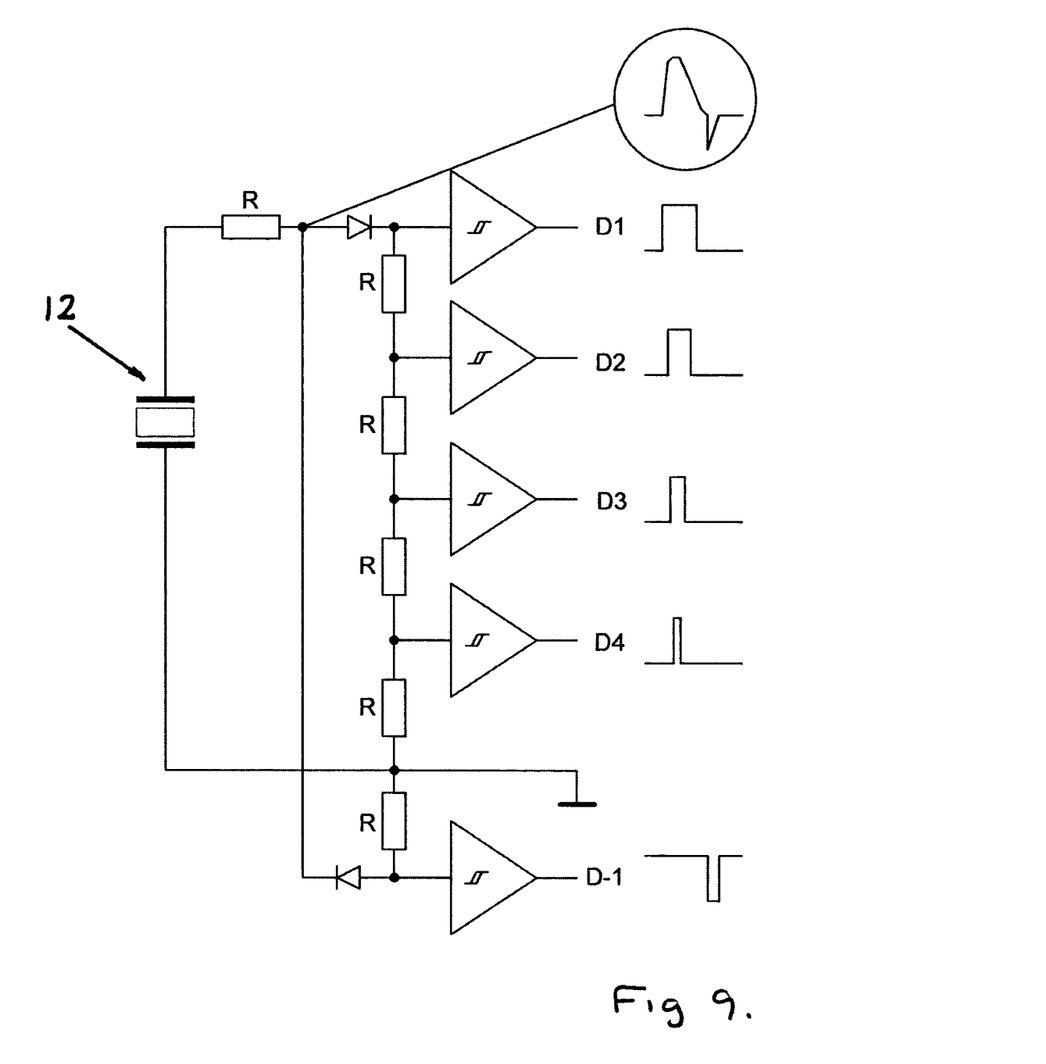
FIG. 9, is a diagram showing a piezo electrical sensor, a divider circuit and electronic switches.

The signal from the piezo is in a first embodiment forwarded to a divider circuit with switching comparators as pictured in FIG. 9. As can be seen the signal from the piezo electrical sensor 12 is forwarded to the divider circuit where the thresholds are detected by the comparators. A typical waveform during a heel-strike and heel-lift event is showed at the input of the divider circuit and corresponding to this the comparators will produce a pulse with a pulse length that corresponds to the voltage level. Using this input as an interrupt for the microcontroller will enable the microcontroller to store timestamps on the event for calculation on the event and determine the type of gait event ongoing. If the patient is just shifting the weight from one leg to another the time between the interrupts is expected to be longer and the amplitude of the signal is expected to be lower. Contrary to this performing a gait cycle the heel-strike event will show a very quick rising signal with short time between the interrupts which in a similar way can be recognized and interpreted by the microcontroller. Thus it is possible to determine if neurostimulation have to be carried out or the person is just standing and shifting the weight from one leg to another. The divider circuit is especially appreciated since the switches in the form of comparators can be carried out in CMOS which has very low power consumption. Thus the switching is done by hardware providing an interrupt for the microcontroller allowing the microcontroller predominantly to be in a power saving sleep mode where a minimum of electrical power is consumed. The electrical supply of the comparators can be the piezo electrical sensor where a part of the energy is supplied to a storage. Adding more layers of piezo electrical foil one or more layers can be reserved for signaling and energy harvesting with the perspective of supplying the entire trigger device partly or fully with energy.

Figure 10:
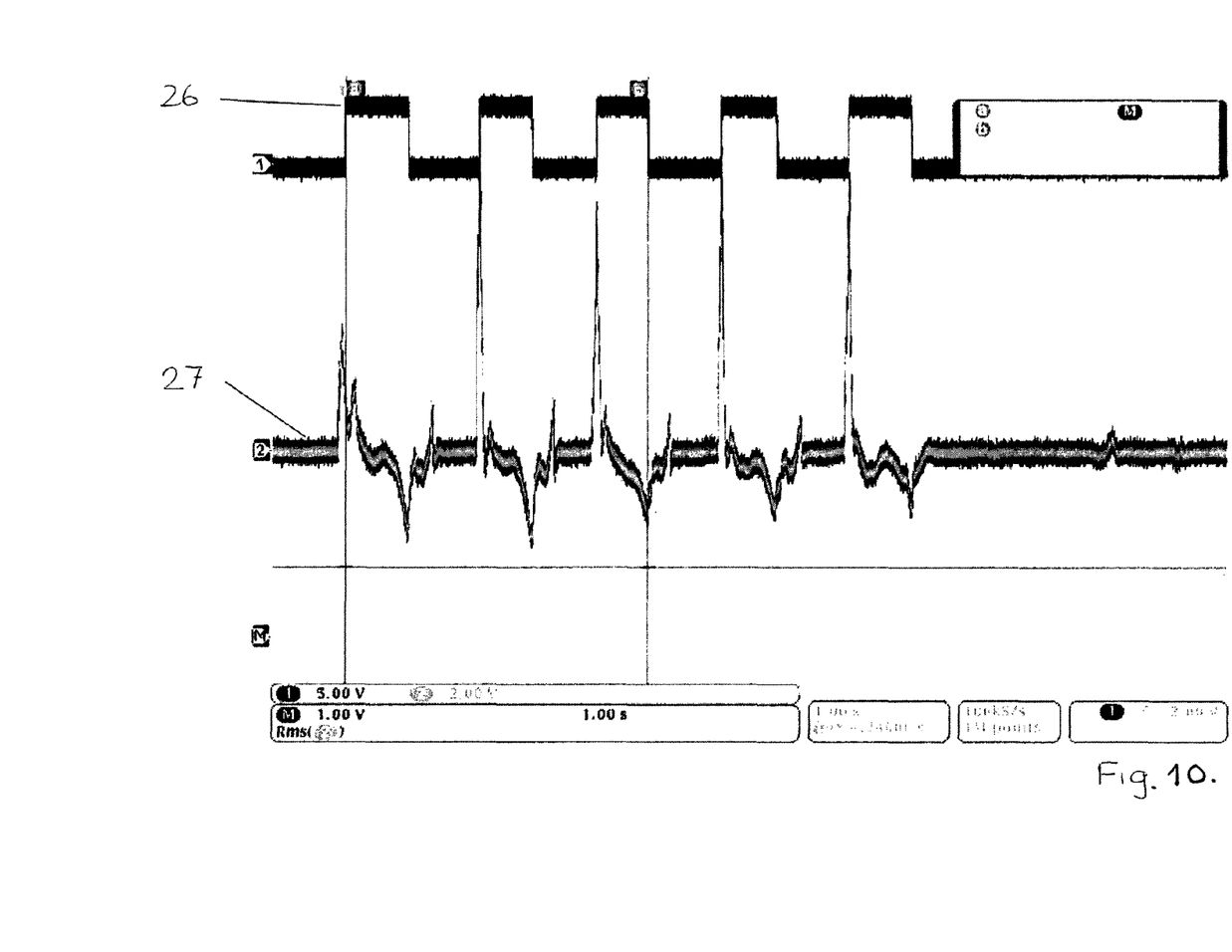
FIG. 10, is a graph, showing a measurement made on a physical embodiment of the trigger device featuring a piezo electrical sensor and a tactile switch, the trigger device being worn by a walking patient

Practical measurements on the embodiment shown in FIG. 5 are provided in FIG. 10. The first waveform 26 corresponds to the signal from the tactile switch. The second waveform 27 pictures the corresponding signal from the piezo electrical sensor 12. The sensor used is a disc shaped piezo electrical sensor of the type 7BB-35-3 from company muRata looking into an impedance of 43 kohm (forty three kilo ohms). The waveform puts confidence in using the signal for determining the heel-strike and heel-lift signals without the need for a mechanical activated switch. As it can be seen in the positions of the marker a, and b, the switch indicated events are met with corresponding measures from the piezo electric sensor clearly indicating the heel-strike and heel-lift events. The system will further benefit of using the voltage divider configuration for providing interrupt signals at selected threshold values and thereby achieving a low power consumption of the microcontroller.

Figure 11:
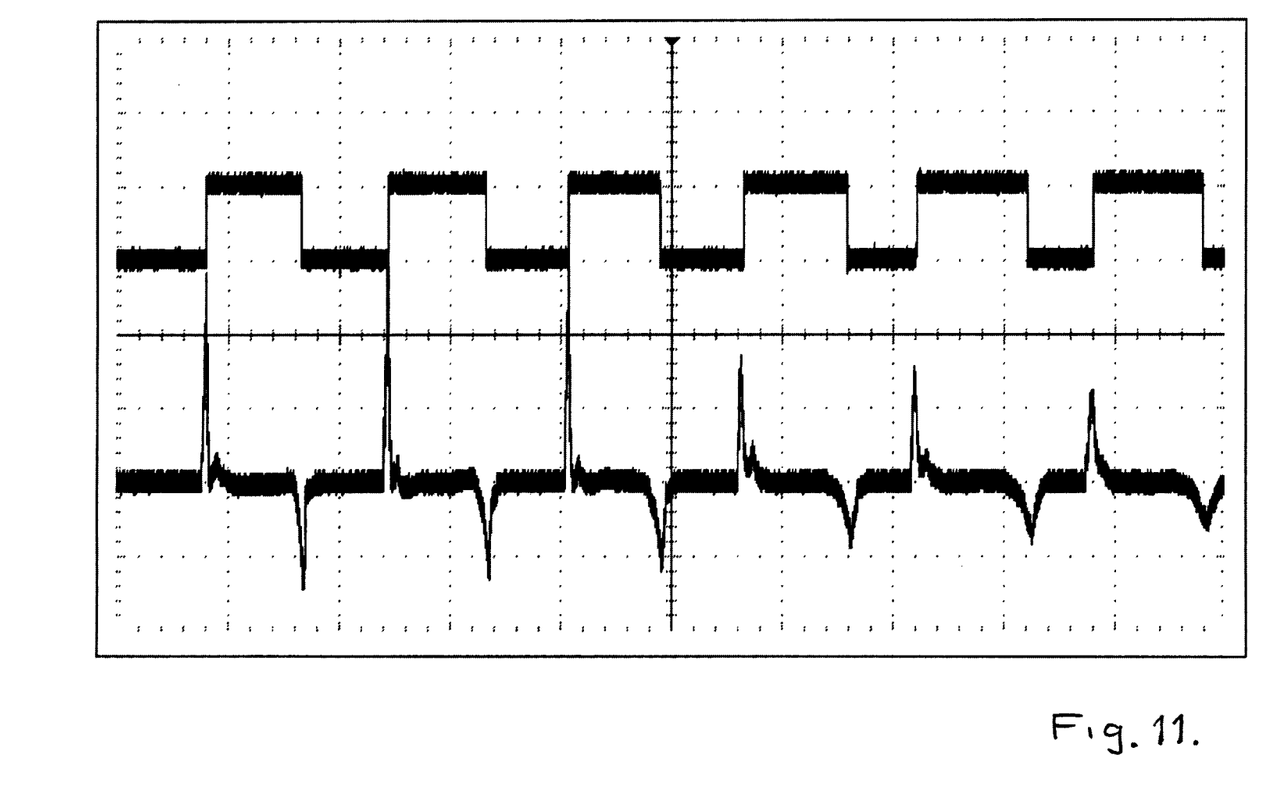
FIG. 11, is a graph, showing a measurement made on a physical embodiment of the trigger device featuring a piezo electrical sensor and a tactile switch, the trigger device being worn by a patient that moves the weight side wards from leg to leg.

A further measurement on the embodiment shown in FIG. 5 is provided in FIG. 11. As can be seen the first three foot flat phases are recorded during walk and the last three are recorded when the patient stands still and are pulling the weight side wards from one leg to another. It is possible unambiguous to distinguish between the two different events and setting up a suitable threshold level for filtering and initiating stimulation exclusively during the gait swing phase.

The invention claimed is:

1. A system for stimulation of nerves comprising:
   at least one electrode,
   a programmable controller equipped with a pulse generator for generating a pulse pattern to be forwarded to the at least one electrode implanted in the corpus of the living being and/or at least one electrode for surface stimulation of nerves or muscles, the controller being equipped with a wireless receiver for wirelessly receiving a wirelessly broadcasted signal from a trigger device for adjusting the timing of the pulse pattern,
   a trigger device including a wireless transmitter for communicating with the controller,
   wherein
   the trigger device is equipped with switching means for sensing at least the events where a first threshold of load and a second threshold of load is exceeded.

2. A system according to claim 1, wherein the switching means are at least a first mechanical activated electrical conducting switch configured for being activated when a first threshold of load is exceeded and a second mechanical activated electrical conducting switch configured for being activated when a second threshold of load is exceeded.

3. A system according to claim 1, wherein the switching means are at least one mechanical activated electrical conducting switch for being activated when a first threshold of load is exceeded where the trigger device is further equipped with a sensor for sensing at least the event where a second threshold of load is exceeded.

4. A system according to claim 1, wherein the first threshold of load is configured to be a load corresponding to a weight less than a person and the second threshold of load is configured to be a load corresponding to a weight close to or slightly over the weight of a person.

5. A system according to claim 1, wherein the switching means for sensing events is at least one electronic switch which is supplied with a signal from a sensor.

6. A system according to claim 1, wherein the switching means for sensing events is a number of electronic switches which are arranged in a voltage divider circuit which is supplied with a signal from a sensor.

7. A system according to claim 3, wherein the sensor is a piezo electrical sensor.

8. A system according to claim 1, wherein each voltage level in the divider circuit represented by the corresponding electronic switch are forwarded to the microcontroller and serve as 1) an interrupt signal when the switch is toggled to change the microcontroller from a sleep mode to an active mode; 2) to store in memory the timestamp of the event; 3) to start calculating the time between the rise and fall of the signal at that specific threshold level; 4) an interrupt signal, when the switch is toggled back to the relaxed or low position, to store in memory the timestamp of the event.

9. A system according to claim 1, wherein at least one voltage level in the divider circuit represented by the corresponding electronic switch are forwarded to the microcontroller and serve as 1) an interrupt signal when the switch is toggled back to the relaxed or low position, change the microcontroller from the active mode and to a sleep mode where no power or a minimum of power is consumed.

10. A system according to claim 1, wherein the energy content in the piezo electric sensor generated signal is used for fully or partly powering the electronic switches or comparators.

11. A system according to claim 1, wherein specific values of thresholds, e.g. the first threshold of load and the second threshold of load, can be adjusted to the weight of the person using the system, by running a configuration program that based on measurements during a gait swing phase determines the appropriate thresholds, configures the system and stores the values in memory.

12. A system according to claim 1, wherein the trigger device includes a number of piezo electrical sensors arranged with the trigger device in such a way that when the trigger device is attached to the foot said piezo electrical sensors are distributed over the area of the foot, the piezo electrical sensors forming a network to provide information on the timing and pressure applied to specific points on the foot during the gait, in order to give input to the system for stimulating the appropriate nerves that corrects the foot drop and thus achieve a more natural swing and gait phase.

13. A system according to claim 1, wherein the piezo electrical sensor, preferably formed on a film, is arranged on top of the dome of a tactile switch, the switch providing a signal corresponding to the exceeding of the first threshold of weight and the piezo electrical signal being compared to a threshold corresponding to the exceeding of at least a second threshold of weight provides a signal to reflect the exceeding of the second threshold of weight, as an input for determining if electrical nerve stimulation has to be initiated.

14. A system according to claim 1, wherein the trigger device includes a mechanical dampening means, eg. a flexible plate or a holding arrangement, that takes at least a part of the load away from acting in the line of force through the sensor, for adjusting the first threshold of load and the second threshold of load to fit the weight of the person using the system.

15. A system according to claim 1, wherein the timing between meeting the first threshold of load and until meeting the second threshold of load is measured and the system is adapted to determine on the basis of the timing measurement if the person using the system is performing a gait swing phase or moving the weight between the legs and then exclusively carry out neurostimulation when the person is performing a gait swing phase.

* * * * *